United States Patent [19]

Buckberg et al.

[11] Patent Number: 5,011,469
[45] Date of Patent: Apr. 30, 1991

[54] PERIPHERAL CARDIOPULMONARY BYPASS AND CORONARY REPERFUSION SYSTEM

[75] Inventors: Gerald D. Buckberg; James V. Maloney, Jr., both of Los Angeles; Kenneth A. Jones, Lake Elsinore; Weldon D. West, Mission Viejo, all of Calif.

[73] Assignee: Shiley, Inc., Irvine, Calif.

[21] Appl. No.: 237,969

[22] Filed: Aug. 29, 1988

[51] Int. Cl.$^5$ .......................................... A61M 37/00
[52] U.S. Cl. ........................................ 604/4; 604/8; 604/53
[58] Field of Search ....................... 604/4-8, 604/50-54

[56] References Cited

U.S. PATENT DOCUMENTS 3,513,845  5/1970  Chestnut et al. ................... 604/4
4,546,399  9/1985  Litziel et al. ...................... 604/4

OTHER PUBLICATIONS

"Regional Blood Cardioplegic Reperfusion During Total Vented by Pass Without Thoracotomy: A New Concept", Okamoto M. D. et al., Journal Thoracic and Cardiovascular Surgery, Sep., 1986 pp. 553–563.
Copy of Front Page and Page 150 of Manual on Artificial Organs, vol. II, The Oxygenator, Yukihiko Nose, M. D., Ph. D.
Copy of Front Page and pp. 298 and 299 of Artificial Lungs for Acute Respiratory Failure, Theory and Practice.
The Journal of Thoracic and Cardiovascular Surgery, Sep. 1986.
Pp. 23–27 of Article Entitled "A New Method of Para--Corporeal Left Ventriculo-Aortic Bypass".

Primary Examiner—Randall L. Green
Assistant Examiner—Randy Shay
Attorney, Agent, or Firm—Knobbe, Martens, Olson & Bear

[57] ABSTRACT

A method and apparatus to arrest or reverse heart damage from myocardial infarction by using a peripheral, femoral-femoral full bypass along with the venting of the left ventricle wherein the rate at which blood is drawn from the femoral vein and the rate at which the left ventricle is vented are related in a predetermined manner. The damaged area is treated with a cardioplegic solution; the blockage causing the heart attack is then removed by a thrombolytic solution or by angioplasty, while blood is prevented from entering the ventricle and from reactivating the heart from its at-rest condition. Normal blood flow is then restored, and the various catheters and bypass mechanisms removed. The system is also useful for peripheral cardiopulmonary bypass systems not involving the application of a cardioplegic solution. The catheters are specially designed for their function.

35 Claims, 7 Drawing Sheets

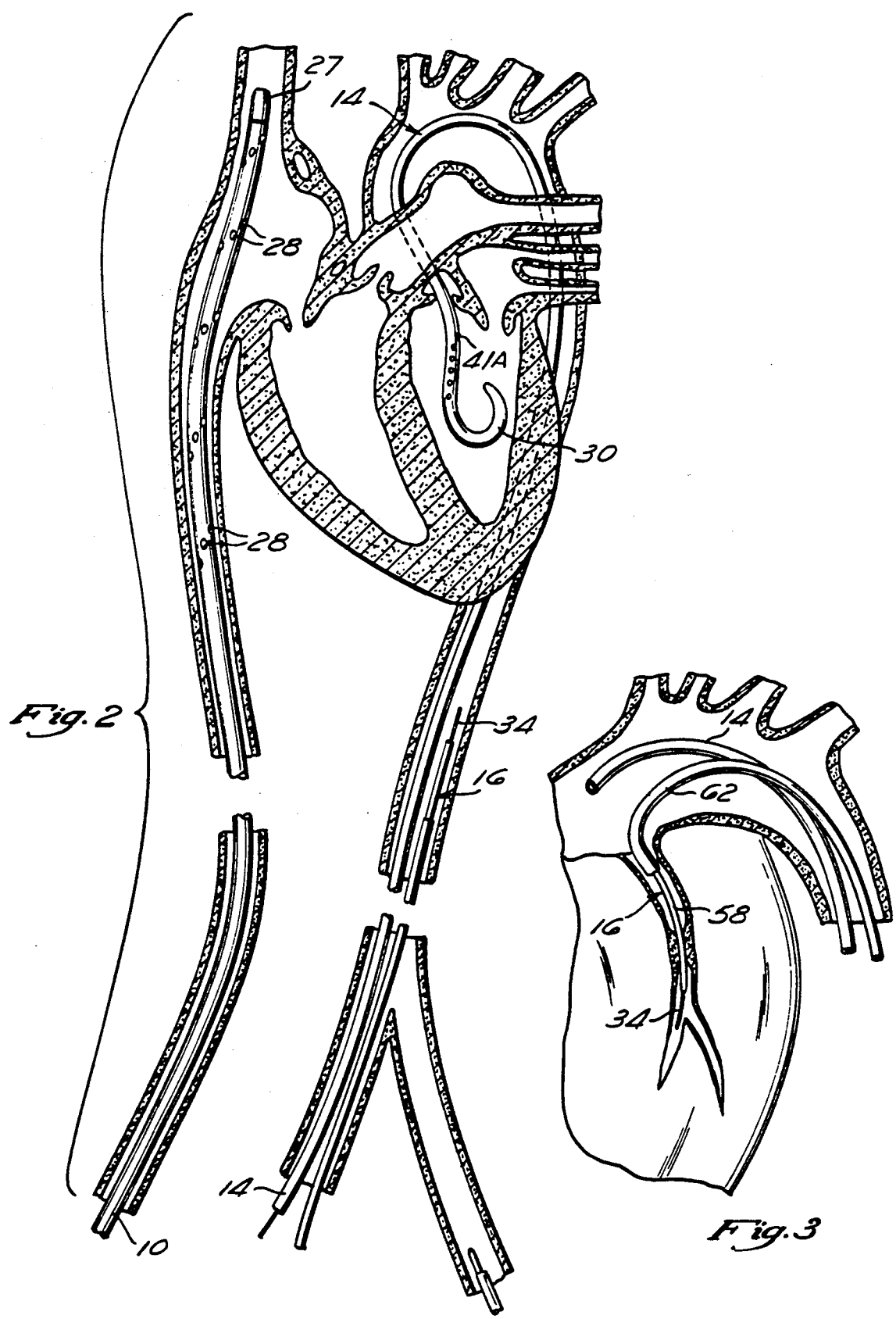

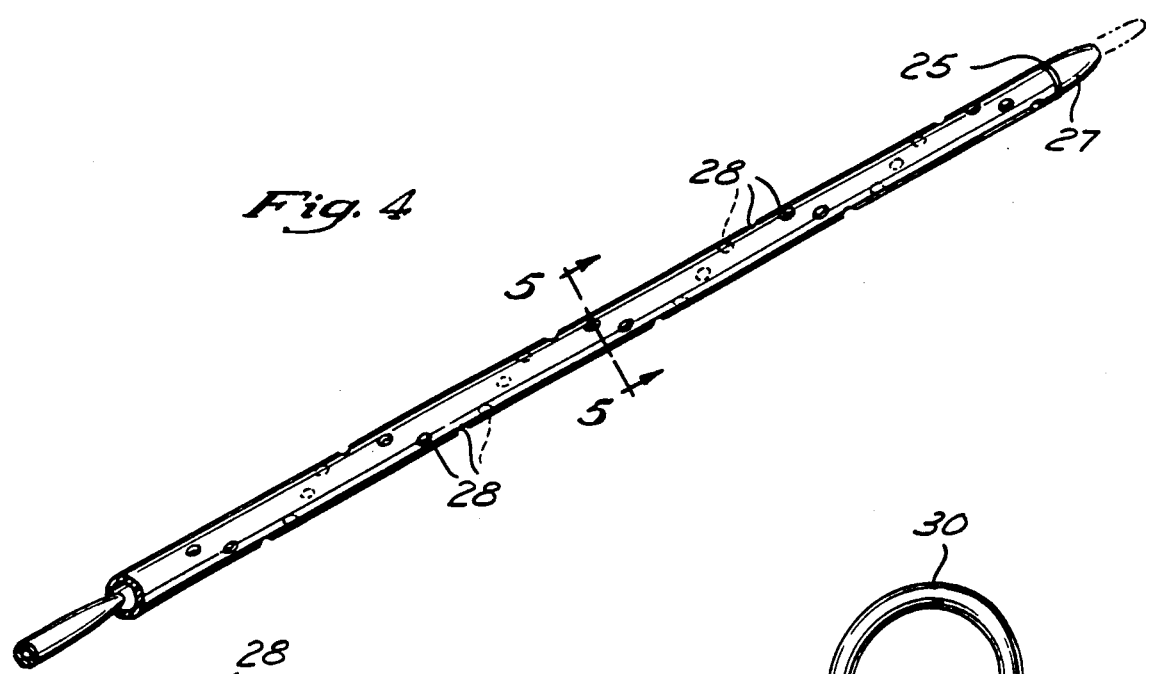
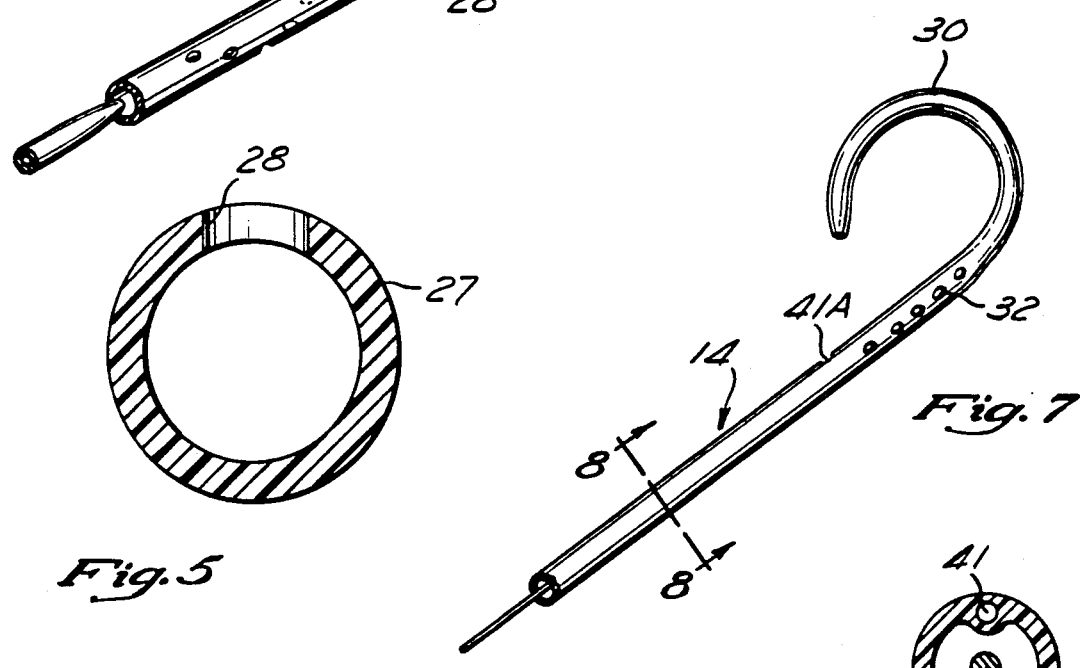
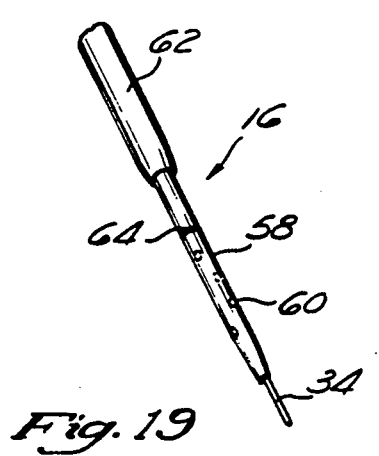
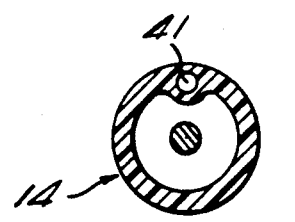

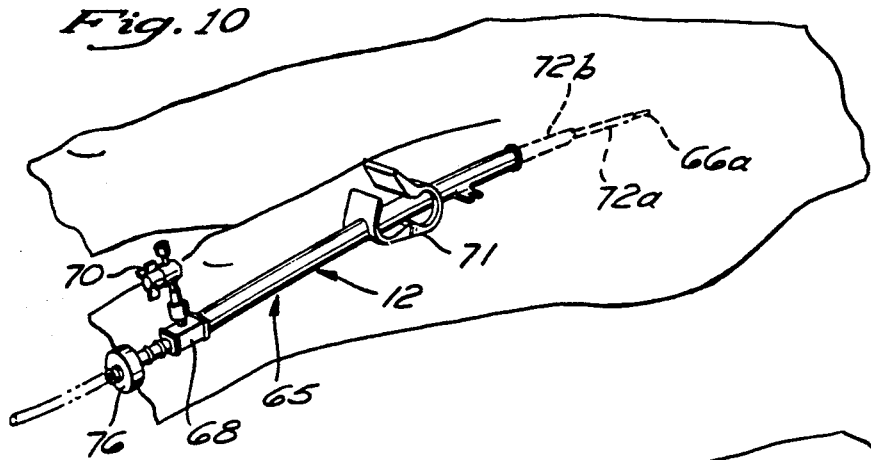
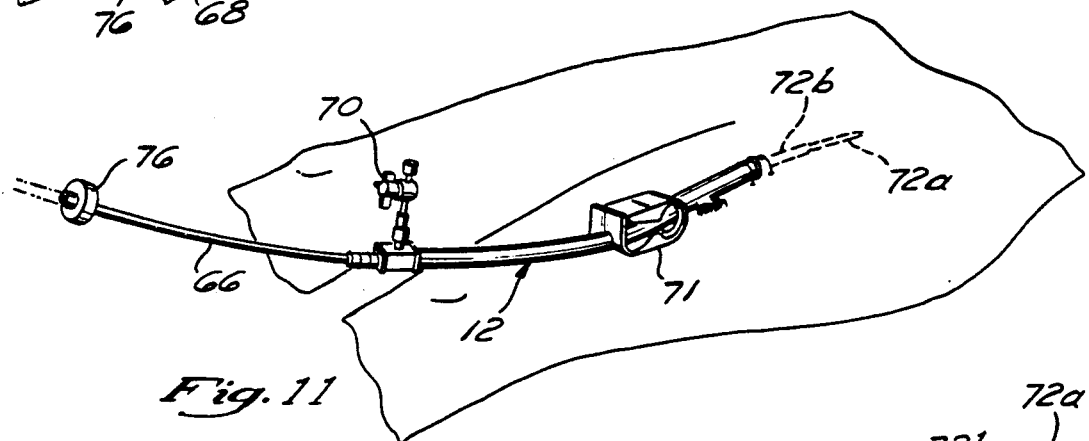
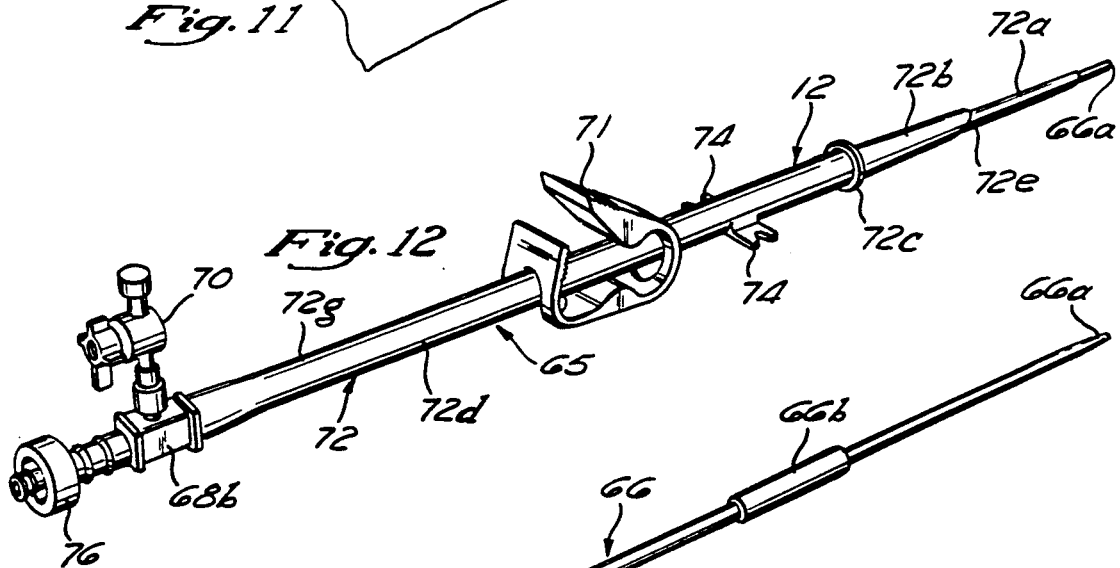
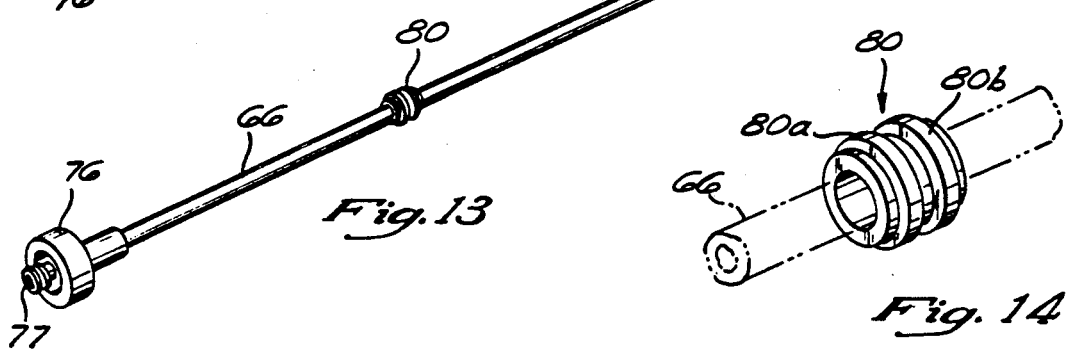
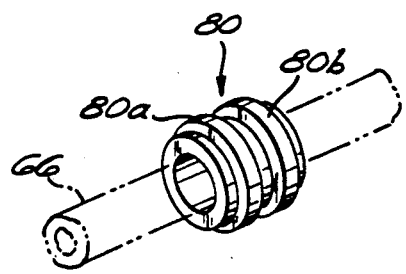

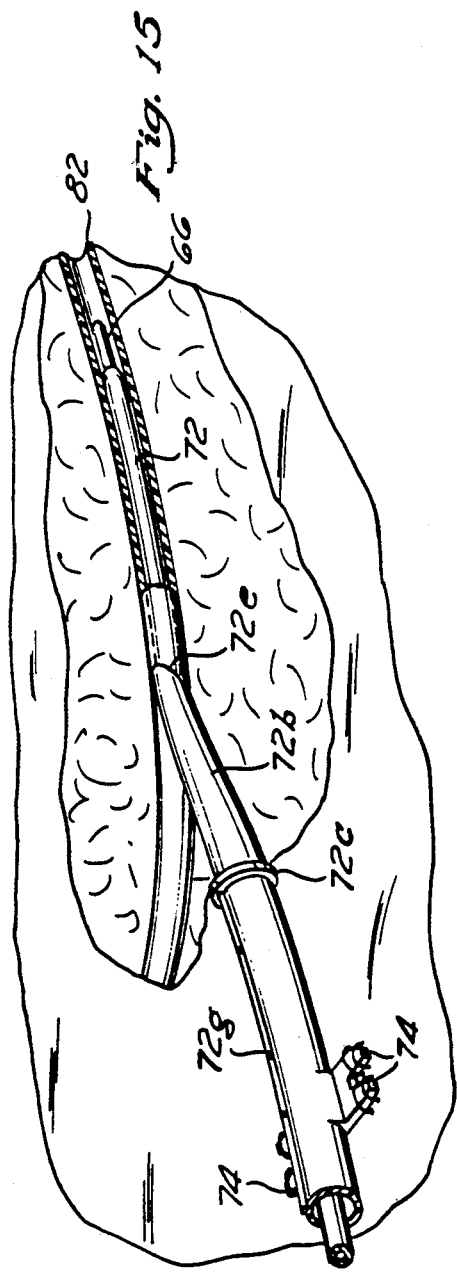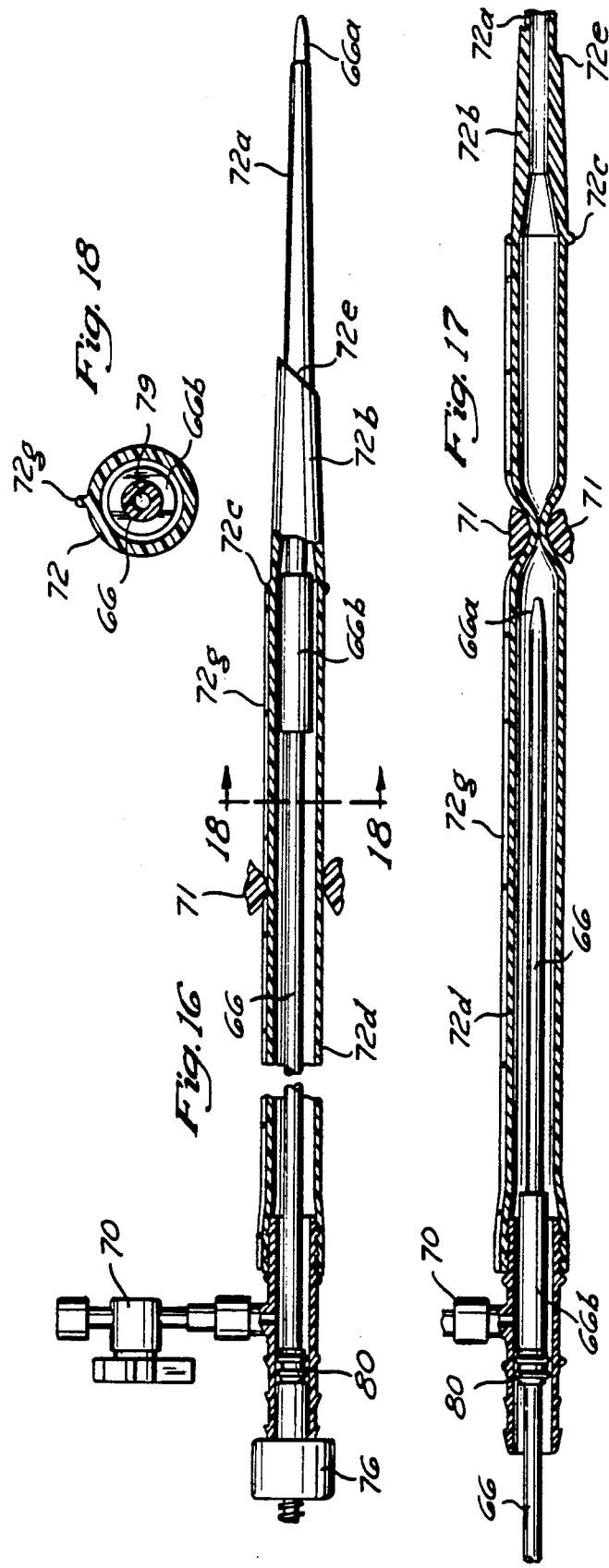

PERIPHERAL CARDIOPULMONARY BYPASS AND CORONARY REPERFUSION SYSTEM

FIELD OF THE INVENTION

The subject invention relates to the treatment of heart attacks by placing the patient on a heart/lung machine without the necessity of a conventional open-chest operation, and to the treatment of the heart attack by the infusion of a special solution directly into the coronary arteries supplying the heart muscle.

BACKGROUND OF THE INVENTION

Each year numerous people suffer a heart attack (acute myocardial infarction) due to the obstruction of a coronary artery which supplies blood to the heart muscle. Of this number, a significant percentage die before reaching medical attention. Another group succumbs after reaching the hospital. Of those which survive, more than half suffer permanent loss of a portion of the heart muscle owing to the damage done during the period of a heart attack by the lack of blood supply (ischemia). This damage impairs the quality of life, shortens life expectancy, and increases the probability of death with subsequent heart attacks.

Currently the methods of treatment of heart attack victims include:

(1) observation and medication in a coronary care unit;

(2) thrombolysis - dissolving by drugs the clot which blocks the coronary artery;

(3) percutaneous coronary angioplasty (PTCA) reopening the obstructed artery with a balloon dilator threaded through the arterial system;

(4) emergency operations for coronary artery bypass-detouring blood around the blockage with a blood vessel graft;

(5) balloon counterpulsation - relieving about 10–15 percent of the work of the heart with a pulsating balloon placed in the body's main artery, usually used as a temporizing measure prior to or during the foregoing methods of treatment; and (6) assist devices - tubes temporarily left in the heart following a bypass operation where the heart is too weakened to support the circulation, even with the balloon treatment of (5) above.

Despite the best available therapy, a significant percent of the patient's die, and those who are not treated fairly promptly suffer permanent loss of heart muscle supplied by the blocked artery. The primary damage to the heart muscle during a heart attack occurs because of the blood supply to a portion of the heart being interrupted; and therefore, the primary goal of the treatments referred to above has been to restore the blood supply as quickly as possible. However, while some of the methods outlined above have decreased the time required to restore blood flow to the portion of the heart subjected to ischemia, they have not resulted in that heart muscle being able to restore its function to the degree previously hoped. Recent studies show that limitations of previous techniques of reperfusion to restore heart muscle function are due to their inability to control the conditions of reperfusion (for example, the blood pressure, the work of the heart) or the composition of the reperfusate blood. The solution used for this purpose keeps the region of the heart muscle from beating (cardioplegia) to minimize its need for oxygen. The cardioplegic solution contains oxygen because it is mixed with oxygenated blood from the heart/lung machine (blood cardioplegia).

Recent experimental studies have demonstrated that controlled reperfusion, which can be achieved via surgical intervention, may facilitate recovery of the left ventricular function after myocardial infarction to a greater degree than can be achieved using conventional pharmacologic or mechanical strategies. The September 1986 issue of the *Journal of Thoracic and Cardiovascular Surgery*, entitled "Studies of Controlled Reperfusion After Ischemia," discloses results of laboratory experience supporting the conclusion that controlled reperfusion is necessary. More specifically, it has been determined that damage can be avoided by administering a special blood cardioplegia reperfusate to the damaged area before normal blood flow is resumed. Tests on dogs and other animals indicate that the blood cardioplegia negates the adverse effects of toxins which build up in the myocardium during the ischemia caused by the obstruction of blood to that portion of the heart. The re-introduction of normal blood flow, without the cardioplegia, does not revive the oxygendeprived tissue and results in loss of all or a portion of the affected myocardium. It appears that the cardioplegia solution flushes the damaged capillary bed of toxins that have accumulated during the infarct episode. This cleansing apparently facilitates the recovery of the heart tissue when normal blood flow is resumed. Included in this issue is a preliminary series of patients treated by surgically controlled reperfusion who experienced the same excellent recovery of heart muscle function that occurred under experimental conditions. These results have been confirmed in a recent series of patients who were treated in a multi-center trial of thrombolytic treatment (TAMI) and who did not qualify for or failed the more conventional pharmacologic approach of thrombolysis. The surgical treatment was that of controlled reperfusion following the protocol described in the September 1986 Journal referenced above.

In addition, the studies referred to in the above-mentioned Journal have shown that the foregoing treatment produces good recovery only when the heart is decompressed (left ventricle vented) by extracorporeal circulation. Without such venting during the extracorporeal circulation, there can be sufficient blood returned into the ventricle to cause it to eject, and thereby raise the metabolic demands of the damaged muscle by stretching it.

The studies reported in the above-referenced Journal utilized open-chest techniques for the extracorporeal circulation, with a secondary pump for the venting of the ventricle to obtain the desired decompression condition. However, it is suggested that instead of an open-chest operation, a peripheral bypass technique be employed wherein catheters are connected to the vascular system. With a peripheral technique, catheters may be introduced percutaneously or by using a cutdown procedure along with vessel dilation.

The aforementioned Journal article (page 560) proposes an experimental model of a peripheral (in this case) femoral-to-femoral vented bypass system in humans, together with regional cardioplegia reperfusion, without thoracotomy. This, however, is a desired goal, and the specific manner and apparatus of accomplishing this is not disclosed in detail because it had not been done.

There have been some femoral-to-femoral bypass systems, such as in U.S. Pat. No. 4,540,399, but it is not clear that total bypass is obtained, and there is no provision for ventricular venting.

Summarizing some of the foregoing background, it can be simply stated that: heart attacks are caused by closed coronary arteries; opening an artery does not cure the heart attack; and controlling the conditions and composition of the initial reperfusion of a blocked coronary artery does permit salvage of the damaged myocardium beyond the obstruction. The only accepted way to control the conditions and composition of coronary reperfusion of individuals undergoing a heart attack is by open-chest surgical operation with direct decompression of the heart, decompression of the left ventricle and direct infusion of the coronary arteries through surgically connected saphenous vein grafts. Although the results of this approach have been proven superior to results obtained by any of the current methods of treating acute myocardial infarction, the performance of a major operation has risks of mortality and morbidity, and a high level of expense.

There is thus a clear need for an improved system which will minimize the damage to the myocardium following heart attacks. Such a system should be able to be applied quickly after the onset of symptoms. It should provide for the opening of the blocked artery without permitting normal blood flow to enter the ischemic area. It should permit infusion of a fluid of a specific composition under controlled conditions of temperature, pressure and flow. Further, the system should relieve the workload of the heart by supporting the body on an extracorporeal circulation to eliminate the flow work of the heart and relieve the left ventricle of all blood to eliminate pressure work of the heart. Further, it is highly desirable that the foregoing be accomplished without the risk of a major chest operation in critically ill patients.

It is also desirable that an improved extracorporeal circulation system be available for applications other than in connection with cardioplegia reperfusion.

SUMMARY OF THE INVENTION

The invention comprises a unique cardiopulmonary bypass system, method and apparatus, including a venous catheter for insertion into a femoral vein and an arterial cannula for insertion into a femoral artery. An arterial pump and oxygenator are connected between the venous catheter and the arterial cannula to circulate all of the patient's blood. A vent catheter is inserted preferably through a femoral artery and passed backwards through the arterial system to the left ventricle of the heart where it removes bronchial blood and permits complete rest to the ventricle. Preferably, the vent catheter is connected in parallel with the venous catheter and is connected in the same line to the pump. With this arrangement, negative pressure developed by the pump is simultaneously applied to the venous catheter and the vent catheter in a manner such that all of the patient's blood which would normally return to the heart is bypassed through the venous catheter, and the blood reaching the left ventricle of the heart is withdrawn through the vent catheter so that the ventricle is decompressed. This is in contrast to previous techniques of ventricular decompression which have required a separate pump to aspirate blood from the left ventricle.

The venous catheter is of special design which, for the first time, permits the induction of percutaneous total extracorporeal circulation, without producing dangerous increases in negative pressure. The hydrodynamics of the venous catheter system are selected so that they permit full normal cardiac output of 5 to 7 liters per minute without exceeding a maximum negative pressure, or suction, in the range of 140 to 200 mm Hg. This constraint minimizes blood damage and avoids creating bubbles in the blood.

Likewise, the vent catheter is carefully sized to handle the volume needed to ensure that the ventricle remains decompressed while operating within the same upper negative pressure limitation. This volume ranges from 50 to 500 ml per minute. The cardioplegia treatment is effective only if the heart is decompressed completely (total vented bypass). Left ventricular decompression is not possible by arterial and venous cannulation alone, as the venous cannula may fail to collect all of the venous return, and some blood from the lungs may enter the left ventricle via the bronchial veins. Connecting the venous return catheter and the vent catheter conduits in parallel to a single pump facilitates monitoring and maintaining the negative pressure below the maximum permitted.

Preferably, the vent catheter includes a separate lumen for continuous monitoring of ventricular pressure to ascertain that the heart is at rest. The vent catheter is specially designed to be inserted through the aortic valve without injury to the valve or producing insufficiencies by distorting the valve. Also, the pressure lumen inlet is located spaced from the catheter tip so that when the lumen inlet is in the ventricle, the attendant knows the vent catheter holes are in the ventricle.

To accommodate possible fluctuations in the volume of the flow required, and to regulate the blood volume of the patient, a reservoir, preferably compliant, is provided bridging the pump, with an inlet to the reservoir being connected to the pump outlet, and an outlet from the reservoir being connected between the venous catheter connection and the pump. Inflow and outflow valves in the connections permit circulating blood volume and therefore blood flow rates to be controlled.

The arterial catheter employs an angled shoulder which limits insertion of the cannula and provides a seal with the artery. Also, it includes a removable seal which prevents hemorrhage from the femoral artery as the stylet within the cannula is withdrawn.

For use of this system in a heart attack situation, there is provided a blood cardioplegia delivery system having an inlet connected to the output of the arterial pump. The coronary reperfusion catheter connected to the output of the pump is inserted through an artery to reach the area of the heart that has been deprived of blood. The reperfusion catheter traverses a clot in a coronary artery narrowing (stenosis) to allow precise control of the reperfusate blood composition and conditions (i.e., flow and pressure). Cardioplegia solution is then supplied to that area while the bypass system is in operation, including maintaining decompression of the ventricle. Following the cardioplegia application, the normal blood flow may be resumed, and an angioplasty can be performed to relieve the narrowing in the coronary artery.

The femoral-femoral bypass system is particularly versatile in that it can be employed in a cardiac catheterization laboratory, since it does not require an open-chest operation. This is very advantageous in connection with patients who would not likely survive the initiation of anesthesia or the opening of the chest for conventional heart surgery under emergency circumstances. With the system apparatus on a cart, the patient and the system may be transported from the catheterization lab into the operating room for use during open-heart surgery. Previous, less than total bypass, percutaneous systems needed to be discarded when patients were brought to the operating room.

The system is also useful in connection with patients in cardiac shock (providing up to 100% support of the circulation, rather than 15% support as in balloon counterpulsation). The system is also useful for routine extracorporeal circulation situations. The system further advantageously lends itself to electronic and mechanical control systems uniquely designed for performance of total extracorporeal circulation and controlled coronary reperfusion.

BRIEF DESCRIPTION OF THE DRAWINGS

FIG. 2 is a schematic, partial sectional view of the heart and venous and arterial passages to the heart.

FIG. 3 is a partial sectional view of a portion of a human heart with a vent catheter and a reperfusion catheter inserted into the heart;

FIG. 4 is a perspective view of a portion of a femoral venous catheter;

FIG. 5 is a cross sectional view on line 5—5 of FIG. 4;

FIG. 7 is a perspective view of a portion of a vent catheter used in this invention;

FIG. 8 is a cross section of the vent catheter on line 8—8 of FIG. 7;

FIG. 10 is a schematic perspective view of an arterial cannula assembly inserted in the femoral artery;

FIG. 11 is a view similar to FIG. 10, but with a stylet of the cannula assembly partially withdrawn;

FIG. 12 is a perspective view of the cannula assembly of FIGS. 10 and 11;

FIG. 13 is a perspective view of the stylet of the assembly of FIG. 12;

FIG. 14 is a perspective view of an anti-backflow ring of the cannula assembly;

FIG. 15 is an enlarged, perspective, schematic view of the cannula assembly inserted in a femoral artery;

FIG. 16 is a side elevational, partially sectionalized view of the assembly of FIG. 12;

FIG. 17 is a cross-sectional view of the cannula assembly with the stylet partially withdrawn and with the cannula clamped to prevent flow therethrough;

FIG. 18 is a cross-sectional view on line 18—18 of FIG. 16; and

FIG. 19 is a perspective view of the detail end of the reperfusion catheter assembly.

DETAILED DESCRIPTION OF THE PREFERRED EMBODIMENT

Figure 1:
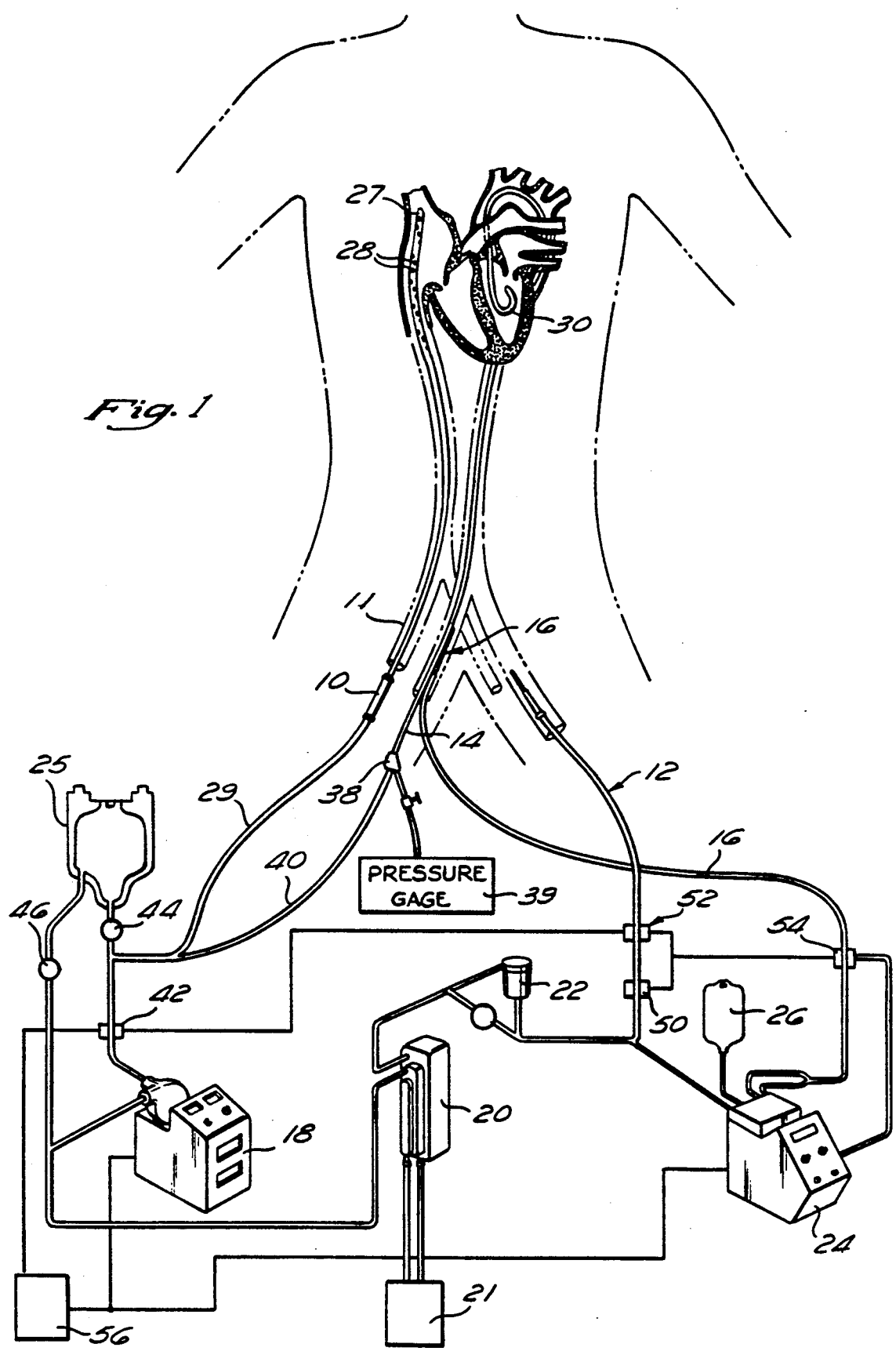
FIG. 1 is an overall schematic view of the system of this invention.

By way of a brief overview the system will be described in connection with FIGS. 1, 2 and 3, as applied to a recent heart attack victim. A femoral-femoral bypass is performed wherein a femoral venous catheter 10 allows right heart access via the femoral vein 11. A femoral arterial cannula 12 allows the return of oxygenated blood to the femoral artery, and is used in connection with the venous catheter 10 to achieve femoral-femoral total extracorporeal circulation.

A left ventricular vent catheter 14 is used to vent the left heart during extracorporeal circulation with the introduction of the catheter 14 made at the femoral artery and passing transaortically into the left ventricle. A coronary reperfusion catheter 16 is inserted into, and transverses a stenosed vessel in order to reperfuse the heart region beyond the stenosis.

The venous catheter 10 and the vent catheter 14 are in fluid communication with an arterial pump 18 which provides a negative pressure in order to draw venous blood into the arterial pump and to draw blood out of the left ventricle, and maintain that portion of the heart in an at rest condition. The arterial pump 18 forces the blood through an oxygenator/heat exchange 20 and an arterial filter 22. A heater/circulator 21 provides fluid flowing into the heat exchanger contained within the oxygenator 20.

A bridging venous reservoir 25 is connected in fluid communication with both the arterial pump 18 and the membrane oxygenator 20 in order to prime the system and to maintain sufficient fluid for proper operation. A cardioplegia delivery pump 24 is in fluid communication with the oxygenated blood after it leaves the arterial filter 22, and is also in fluid communication with a cardioplegia source 26 so as to mix the oxygenated blood and cardioplegia before delivering it at a predetermined flow rate to the coronary reperfusion catheter 16.

The vent catheter 14 removes all residual blood from the left ventricle and enables the heart to maintain an at-rest condition while the reperfusion catheter 16 enables reperfusion of the heart region beyond the stenosis which precipitated the heart attack.

VENOUS CATHETER

In more detail, the femoral venous catheter 10 is preferably made from ethylene-vinyl-acetate (EVA) tubing, preferably having about 18% acetate. The tubing has a constant inner diameter from the insertion tip up to the proximal end. The proximal end of the catheter 10 connects to a ⅜-inch connector which is in fluid communication with the arterial pump. The catheter 10 should be long enough to reach the right atrium from the femoral triangle. An intravascular length about 70 cm, and an overall length of about 85 cm, has been found to be suitable. The thin wall and flexibility of the catheter allow for its introduction percutaneously into the femoral vein of a wide range of patients, and resist the kinking that might otherwise occur with other thin wall catheters as they are advanced through the iliac veins and across the curve of the pelvis.

The distal end 27 of the venous catheter lo, as seen in FIGS. 4 and 5, has a plurality of drainage holes 28 which in a prototype product have a diameter of 0.165 with ¼-inch center to center spacing. These holes have smooth edges and are formed by a tubular cutter, with the catheter internally supported on a mandrel. The holes are arranged in a spiral pattern so that if some holes are blocked by vessel walls, others will be open. This arrangement also minimizes weakening of the catheter while providing the necessary hole area. The holes extend sufficiently far from the distal end of the catheter to span the area from which blood is to be withdrawn. The preferred technique for introducing this cannula into the body is to use the Seldinger technique (percutaneous) or a cutdown procedure along with vessel dilation. A radiopaque tip marker 25 near the distal end enables the drainage holes to be oriented in the superior vena cavae. An elongated removable stylet 31 which receives a 0.045 inch guidewire (not shown) is used to introduce and guide the catheter into position.

The cross-sectional size and the material of the catheter 10 is particularly critical. Since a total bypass system is needed to accomplish the goals of the invention, it is necessary that the venous catheter fit within various constraints. Bypassing the patient's total blood flow requires a capacity in the range of up to 5-7 liters per minute. An overall flow rate of 5 liters per minute is expected in most patients. A thin-walled construction is advantageously used to provide a larger blood flow within the size limitations that may be accommodated by human veins. The EVA material, in connection with the thin-walled construction, provides the needed flexibility to be properly positioned, yet sufficient strength to prevent kinking during normal handling. Moreover, the characteristics of the material are such that if the tubing is kinked and then released, it is self-restoring without significant weakening.

It has been determined that a negative pressure of 200 mm of mercury is an appropriate safe maximum. Higher levels of negative pressure, which could create greater blood flow, run the increasing risk of creating bubbles in the blood. Although a minimum wall thickness is desired, the tubing must not collapse when subjected to such negative pressure. It has been determined that a catheter size of 26 French (O.D. - 0.341 inch, 8.66 mm) is suitable. Preferably, the catheter has an inner diameter of 0.277 inch (7.03 mm), thus making a wall thickness of 0.032 inch (0.825 mm). An alternative approach is to use two smaller venous catheters that will carry the flow at the same negative pressure.

Figure 6:
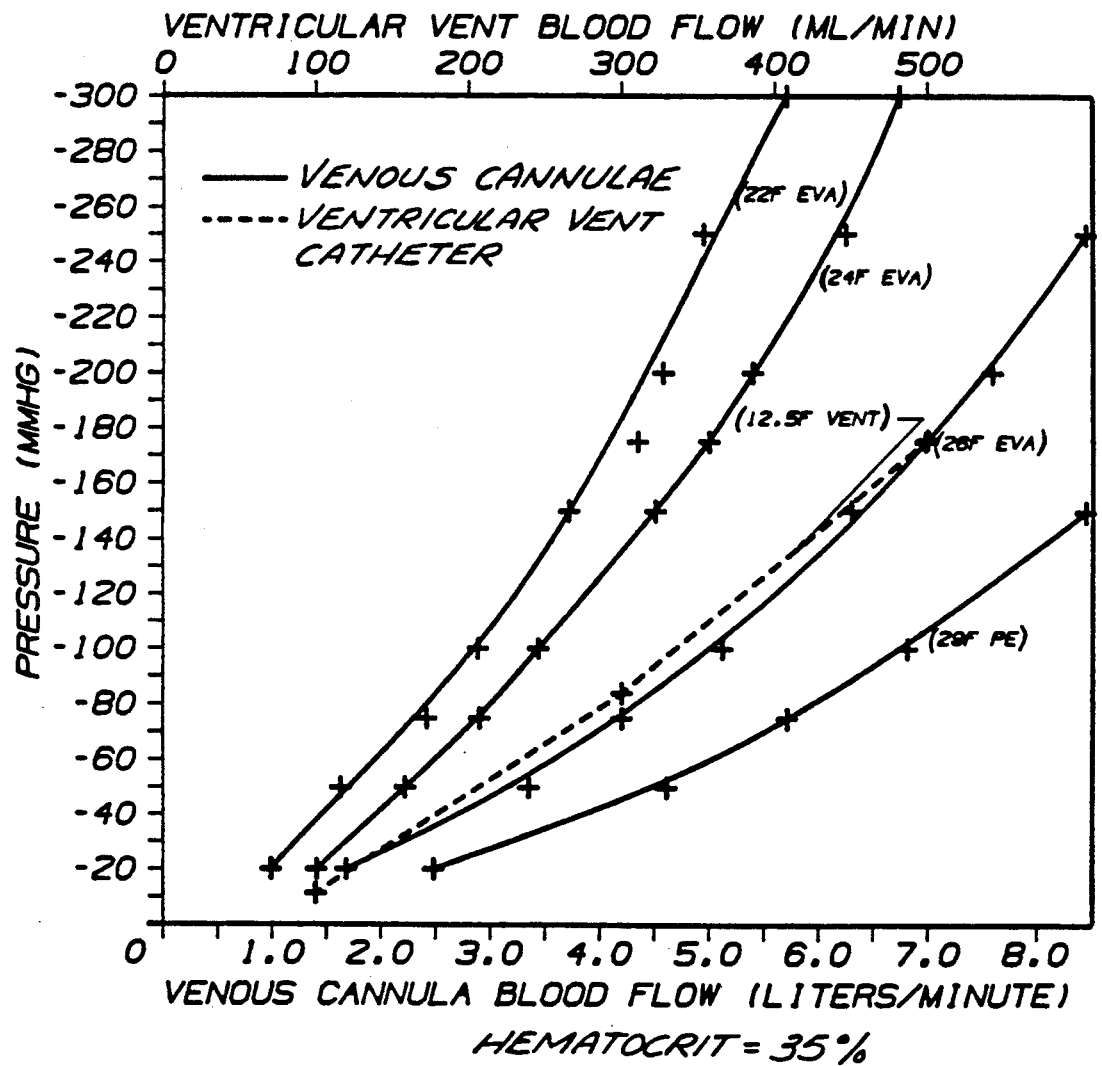
FIG. 6 is a graph illustrating the fluid flow dynamics of the venous catheter and the vent catheter.

FIG. 6 illustrates the constraints of the venous catheter construction graphically from test data. It can be seen that the fluid flow dynamics are such that significant negative pressure is needed to approach the required flow rates, but yet the increased flow from increased suction diminishes quickly at higher levels, particularly for the smaller lumens. Within the acceptable pressure limit, it can be seen that inadequate flow is obtained from a 22F or 24F (French) thin-walled lumen. A 29 French thin-walled size provides adequate flow, but is too large for the vein of some patients, and produces insufficient negative pressure to assist vent drainage optimally (as discussed below). Incidentally, the 29 French lumen was made of polyethylene rather than EVA. It is believed that the flow curve would be similar for EVA. The 26 French size provides adequate flow within an acceptable pressure range of about 100-200 mm Hg, and it can be accommodated by the femoral vein of most adults.

VENT CATHETER

Referring to FIGS. 7 and 8, the vent catheter 14 is preferably a size 12.5 French (0.164 inch, 4.166 mm O.D.) (0.120 inch, 3.04 mm I.D.). The catheter is preferably made from a flexible polyvinyl chloride (PVC) tubing. The distal end 30 is formed in a loop providing a so-called "pigtail." This loop, when unstressed, has an outside diameter of about ⅛-inch, and has a plurality of spaced apertures 32 which are preferably about 0.050 inch in diameter and extend over a vent length of about 4 cm. A series of apertures 32 are located on opposite sides of the catheter.

The catheter 14 must be long enough to reach the left ventricle from the femoral triangle when passed retrograde through the arterial system. A catheter with an intravascular length of 100 cm, and an overall length of about 112 cm is preferred.

As seen from FIG. 8, the catheter 14 includes a pressure monitoring lumen 41 which is integral with and formed in a wall of the vent catheter 14. Preferably, this lumen 41 has a diameter of about 0.030 inch. The lumen 41 extends from the proximal end of the catheter 14 to a pressure inlet 41a which is spaced from the catheter tip a distance further from the tip than the apertures 32. The inlet 41a is positioned about 4 inches from the distal end of the catheter. The inlet 41a is located on the same side of the catheter 14 as the pigtail to prevent obstruction of the inlet 41a when the catheter contacts the ventricular wall.

Preferably, the catheter 14 is extruded with the lumen 41 extending throughout the length of the tubing. After the apertures 32 are formed, the distal end of the tubing is heated and stretched to reduce its diameter and increase flexibility, and to form the pigtail into its curled shape. In the stretching and heating operation, the lumen 41 is closed on the distal end of the catheter. The opening 41a is formed by cutting the tubing at the desired location spaced further from the tip than the apertures 32.

In the stretching of the distal end, the exterior diameter of the catheter is decreased from 0.164 inch to about 0.100 inch, and the interior diameter is decreased from 0.120 inch to 0.062 inch. The very tip of the catheter is reduced a slight amount further. That is, the tip 0.030 inch is tapered on its exterior and is reduced on its interior diameter to about 0.040 inch.

The preferred method of introducing the vent catheter 14 into the femoral artery is by using a sheath introducer procedure. After a tubular sheath (not shown) is positioned in the entrance to the artery, a guidewire 47 is introduced into a stiffening stylet (now shown) that is in the flow lumen of the catheter. The guidewire extends beyond the pigtail distal end 30 sufficiently to straighten it and to permit insertion. The assembly is then inserted through the sheath into the artery. The guidewire and stylet are stopped when the wire approaches the aortic valve. The guide wire and the stylet are then withdrawn approximately 10 cm. As the guide wire and stylet are withdrawn past the distal tip, the pigtail recurls, due to its memory, into the position shown in FIG. 7. Thus, the curled distal end resiliently engages the aortic valve and passes through the valve without trauma when the valve opens. The distal end then assumes the position illustrated in FIG. 2 wherein the pressure lumen hole 41a in the distal end is shielded from the ventricle walls so as to prevent blockage when pressure is monitored through the catheter. The flexibility of the catheter permits its presence in the ventricle, across the aortic valve, without causing distortion of the cusps of that valve and therefore avoids aortic insufficiency.

A tube 40 is in fluid communication with the proximal end of the vent catheter via one aperture in a Wye connector 38 with the tube also communicating with the arterial pump 18. The catheter 14 is sized to allow transmission of approximately up to 500 ml per minute of blood flow at the same negative pressure at which the catheter 11 is operated by the arterial pump 18. A pressure transducer is connected to a second aperture in the Wye connector 38 which in turn is connected to the second lumen 41. Thus, the lumen 41 monitors the pressure in the left ventricle directly. If the ventricle is being properly decompressed, the sensed pressure should be about zero. Thus, there is a significant difference in pressure on the opposite sides of the aortic valve. This can be observed on a pressure monitoring instrument by moving the catheter so that the pressure lumen inlet 41a is exposed to either ventricular pressure or arterial pressure. The location of the inlet 41a is important in that, if the pressure is at the ventricular levels, ejecting or decompressed, it is known that the vent apertures 32 are in the ventricle.

The vent catheter is, as noted, necessary to ensure the left ventricle is completely decompressed, and does not fill with fluid and cause the heart to eject (pump), even though the heart is being bypassed. The venous drain cannula 10 does not ensure continual left ventricle decompression. Some coronary sinus return and/or bronchial flow will enter the left ventricle, distend it, allow wall tension to develop and result in occasional ejection despite apparent right heart decompression from the venous catheter 10. Thus, it is important that the catheter and its connecting tube 40 are sized to transmit the maximum anticipated flow from the left ventricle. This can range from 50 to 500 ml. Further, it is necessary to restrict negative pressure to the 200 mm Hg limitation mentioned above in connection with the venous catheter.

With reference to FIG. 6, the relationship between applied negative pressure (ordinate) and venous cannula flow (lower abscissa) and vent catheter flow (upper abscissa) is presented. Note: (a) The venous flows of 5 to 7LPM are achieved at negative pressures of less than 200 mm Hg only with EVA catheters #26 and #29 French. (b) The 12.5 French vent catheter always drains 7 percent of venous flow, the maximum expected flow from the left ventricle at venous flows of 5 to 7LPM.

FIG. 6 also illustrates the constraints of tubing size and pressure for the vent catheter identified as 12.5F vent on the graph. The curve for the vent catheter shows a vent flow capacity of about 100 ml/minute at a very flow negative pressure, and up to 500 ml/minute at about 175 negative pressure. This is a very satisfactory pressure limit for providing the desired vent flow capacity. As shown in FIG. 1, the suction provided by the venous catheter 10 and the ventricular vent catheter 14 are both advantageously provided by the same arterial pump. The diameter and flow resistance of the tubes 29, 40 and the catheters 10, 14 are selected with a diameter and length to provide a predetermined ratio of flow from each of the catheters for a given suction by the pump. Thus, the amount of suction provided to the left ventricle by the vent catheter 14 will vary in a predetermined relationship with respect to the blood withdrawn from the femoral vein by the venous catheter. While a separate pump can be employed for the vent catheter, as in the prior art, it is highly desirable that the single pump approach be employed. To accomplish this, it is necessary to balance and coordinate those two catheters. That is, it is necessary to utilize a vent catheter that provides the needed flow within the pressure constraints required in connection with the venous flow. Thus, the amount of suction provided to the left ventricle by the vent catheter will vary in a predetermined relationship with respect to the blood withdrawn from the femoral vein by the venous catheter. As seen, the curve for the vent catheter is very similar to that for the 26 French venous catheter in the flow range desired. Thus, if there is a need for change of flow in either catheter, the flow through the other catheter will be satisfactory. With the above specified flow rates, the flow rate of the venous catheter 10 will be, in a preferred construction, about 14 times greater than the flow capacity in the vent catheter 14 for the same negative pressure, but may range from 10 to 50 times greater for tubes of different sizes.

If, in monitoring the pressure in the ventricle, it is observed that the pressure is becoming too high, indicating an accumulation of blood, pump speed can be increased to increase the flow through the vent catheter and the venous catheter, so long as the maximum negative pressure of 200 mm Hg is not exceeded. Thus, for example, if the ventricle pressure should start to climb with vent flow at 360 ml and venous flow at 51, pump speed can be increased to provide 500 ml of vent flow capacity, venous flow only increasing to 7 liter a minute, and the negative pressure is at a safe 180. A venous pressure transducer 42 monitors the pressure in the tubes 29 and 40 generated by the arterial pump 18.

A ventricular vent catheter of the type described above is also useful for reducing volume of the ventricle in partial bypass situations, i.e., when not using a venous catheter and an oxygenator. In such situations a larger catheter is desired, such as 18 French. The inlet holes 32 may also be enlarged to accommodate increased blood flow. Possibly with a larger catheter yet, a 100% assist can be attained.

BRIDGING RESERVOIR

The bridging reservoir 25 is connected in parallel with the arterial pump 18, with flow clamp 44 between the reservoir and the pump inlet, and a flow clamp 46 between the pump outlet and the reservoir. With this arrangement wherein the flow is not through the reservoir, the volume in the circuit can be controlled by temporarily opening one or the other of the clamps. If more volume is needed, the clamp 44 is briefly opened and then closed when the volume is at the desired level. Similarly, if less volume in the circuit is desired, the clamp 46 is briefly opened until the desired volume is attained.

The system and method of this invention is a closed system; the chest is not opened to access the heart and there is no blood-to-air interface (other than in the oxygenator 20). Thus, whatever blood is taken out of the body must be returned to the body via catheter 12. The bridging reservoir 25 facilitates circulatory stability during the initiation and conduct of the bypass by providing volume control. Maintaining a stable fluid flow in the body is especially important during the time immediately following the initiation of extracorporeal circulation, as such instability can cause severe hypotension, possibly exacerbate the infarction, and cause secondary arrhythmias or cerebral symptoms. The reservoir provides sufficient fluid to maintain circulatory stability and has the capacity to allow fluid removal if the patient's blood volume is excessive due to heart failure. Further, the fluid in the reservoir can be used to prime the system.

ARTERIAL PUMP, OXYGENATOR, FILER, BUBBLE DETECTOR

The arterial pump 18 withdraws blood from the body under a negative pressure (suction), along with the appropriate amount of fluid from the reservoir 25, if any is needed, and pumps the blood and fluid mixture out of the pump under a positive pressure. The arterial pump 18 is schematically illustrated in FIG. 1 as a centrifugal pump. Such a pump is known in the art and hence is not described in detail herein. One suitable centrifugal pump is that provided by Biomedicus of Minneapolis, Minn. A primary advantage of a centrifugal pump is that it has "hydrodynamic slippage" such that if the patient's blood volume falls, the blood flow diminishes without producing high negative pressures and creating nucleation ("boiling") of gases as might occur with a displacement pump. The pump is connected to an electronic controller to prevent negative pressure from going above 200 mm Hg.

From the pump 18, the blood is forced under pressure to the oxygenator 20 where the blood is oxygenated and the temperature of the blood is controlled. The oxygenator 20 and heater circulator are known in the art and are not described in detail herein.

From the blood oxygenator, the blood is preferably forced through an arterial filter 22, although a bypass is provided. After leaving the arterial filter 22, the main portion of the oxygenated and filtered blood is directed to the arterial cannula 12 where it is returned to the femoral artery of the body.

A bubble detector 50 and an arterial pressure transducer 52 may be located on the tube carrying the blood to the arterial cannula 12.

Figure 9:
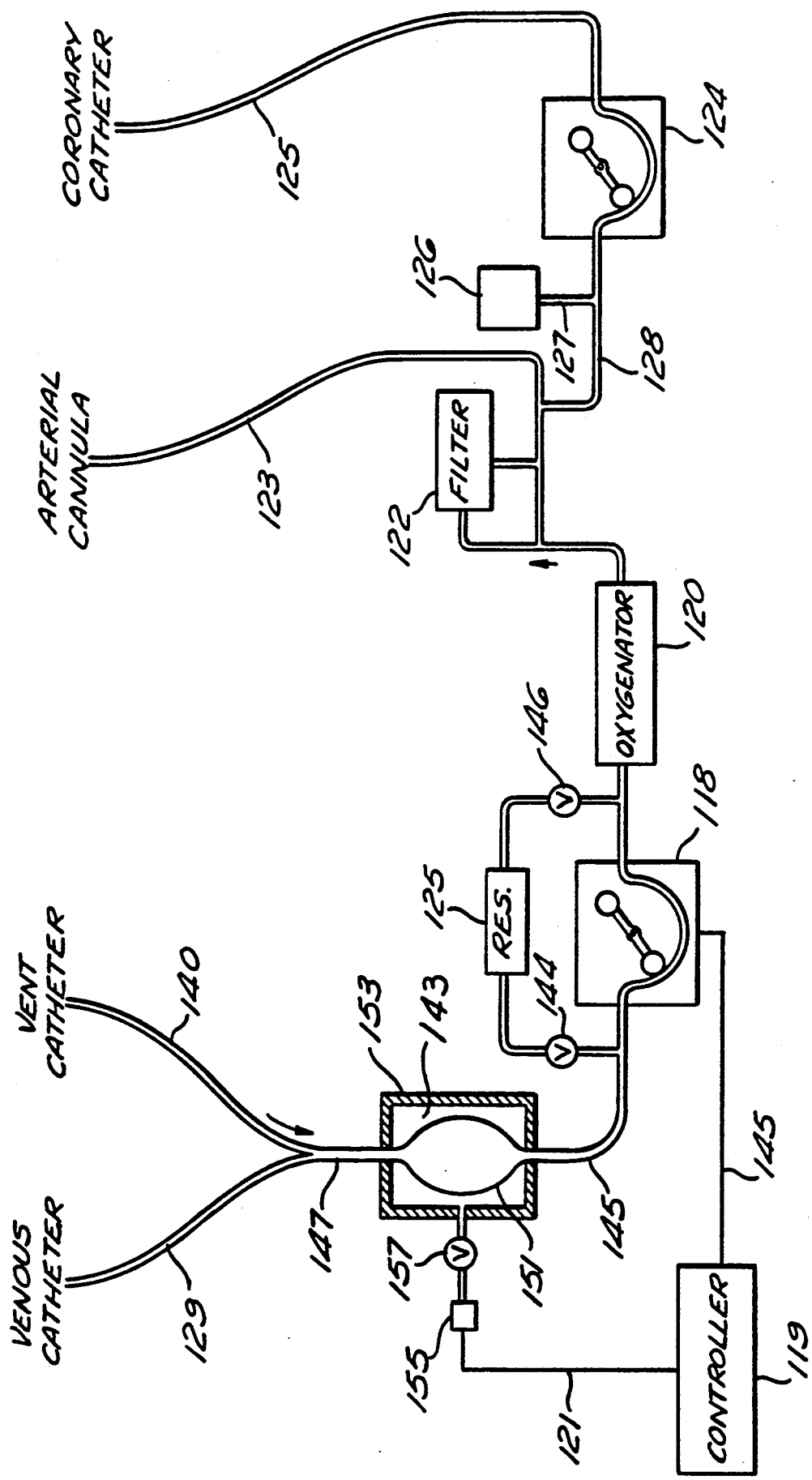
FIG. 9 is a schematic illustration of the use of an alternate pumping arrangement.

In lieu of aspirating blood through the venous catheter with a centrifugal pump, a positive displacement pump may be attached to the venous line with an interposed compliance chamber (to dampen phasic pressure variations) such that a servo based on negative pressure in the venous line achieves the desired flow. Such a system is schematically illustrated in FIG. 9. A venous drainage line 129, and a vent catheter line 140, comparable to the lines 29 and 40 in FIG. 1, are joined at a Y-connection to a common line 141 leading to a compliance chamber 143. This chamber is in turn connected by tubing 145 to a positive displacement pump 118 schematically illustrated as a peristaltic pump. A suitable example of a peristaltic pump is made by Stockert/Shiley, in Munich, Germany. The pump 118 is controlled by an electronic controller 119 which receives pressure feedback from the compliance chamber through a suitable pressure transducer connection 121.

The balance of the system of FIG. 9 is comparable to that shown in FIG. 1. A reservoir 25 with inlet and outlet controls 144 and 146 bridges the pump 118 to provide for volume adjustment. The output of the pump is directed through an oxygenator 120, and optionally a filter 122 to a line 123 leading to an arterial cannula. A portion of the oxygenator output is directed through a line 129 to a cardioplegia pump 124 and conducted through a line 125 to a coronary artery by a suitable perfusion catheter. A cardioplegia supply 126 is connected by a line 127 to the pump 124.

The compliance chamber 143 includes a flexible bladder or reservoir 151, having an inlet connected on one end to the venous drainage line 147 and an outlet connected on its other end to pump inlet tube 145. A rigid outer housing 153 encloses the bladder 151. This housing is sealed around the bladder 151 so that the negative pressure applied to the bladder 151 by the pump 118 is also applied to the space within the housing 153 surrounding the bladder 151. This negative pressure within the housing 153 is, as indicated above, sensed by a transducer 155 and fed back to the controller 119. A valved outlet 157 from the housing 153 is opened to atmosphere during priming to allow the bladder to initially expand due to the head pressure of the fluid in the system. The valve is then closed so that any changes in the size of the bladder are then reflected in pressure changes in housing.

The peristaltic pump 118 is desirable in that the pumping mechanism does not actually contact the blood, thus eliminating a source of contamination and allowing reuse of the pump. Its shortcoming, however, is that if the blood supply falls, the pump can quickly increase the negative pressure applied on the venous drainage line to unsafe levels, even with a pressure sensor in the line to send a signal to a controller, the negative pressure can rise undesirably before the pump speed reacts to reduce pressure. The compliance chamber 143 in combination with a sensor and the pump controller solves this problem. The pressure within the rigid housing 153, being the same as that within the flexible bladder 151, is continually sensed and fed back to the pump controller. Thus, if there is a sudden loss of blood which would result in an increase in negative pressure, the bladder will contract to reduce the rate of the negative pressure rise, giving the controller 119 and the pump time to reduce the speed of the pump 118.

As another variation, the housing 153 can be configured to replace the bridging reservoir 125, including being provided with the necessary inlet and outlet valves or clamps. Similarly, venous return can be augmented by negative pressure applied to the space between the housing 153 and the reservoir 151.

CARDIOPLEGIA PUMP

A portion of the oxygenated blood through the arterial filter 22 is directed to the cardioplegia delivery pump 24. A cardioplegia solution from a cardioplegia source 26 is mixed with the blood and provided under a controlled temperature and pressure to the coronary reperfusion catheter 16. A normal body temperature of 37° Celsius is believed suitable for the reperfused solution. A suitable cardioplegia solution is believed to be an aspartateglutamate-enriched, hypocalcemia, buffered, hypersomolar blood solution, as discussed more particularly in the above-mentioned Journal, Thoracic Cardiovascular Surgery, September 1986.

CONTROLS

A reperfusion pressure transducer 54 and monitor/pump feedback helps regulate the pressure with which the cardioplegia solution is provided to the catheter 16. A flow rate of 50 ml/min or that rate obtained with 50 mm Hg over the pressure drop in the system, whichever is greater, is believed suitable for the reperfusion. Thus, flow is reduced if the pressure exceeds 50 mm Hg, but the rate is best at 50 ml/min if the pressure drops below 50 mm Hg. Further information regarding reperfusion flow rate may be found in Article XVI in the above-mentioned journal. The various pressure transducers 42, 52, 54 and the bubble detector 50 all electronically communicate with a system controller 56, which in turn monitors the vital signs of the heart attack victim and regulates the amount of fluid withdrawn from, and reintroduced to, the victim.

ARTERIAL CANNULA

The femoral arterial cannula 12 is, as shown in FIG. 12, a component of a cannula assembly 65. The assembly further includes a stylet 66, which is slidably received within the cannula, a fitting 68 secured to the proximal end of the cannula, a stopcock 70 on the fitting, and a clamp 71. The cannula 12 which is disclosed in detail in FIGS. 10-18 and below is separately claimed in a copending application since it is useful in systems other than that illustrated in FIG. 1.

The cannula 12 comprises an elongated tubular body 72 preferably made from a medical-grade silicone rubber or a polyvinyl chloride material. The body 72 has three primary sections including a distal tip section 72a for insertion into the femoral artery, an intermediate section 72b adapted to extend from the artery to a raised suture stabilizing ring 72c to be located near the exterior skin of the leg, and an exterior section 72d extending from the suture ring 72c to the fitting 68.

The tip of section 72a is tapered to facilitate insertion into an artery. In a preproduction version of the cannula, the exterior diameter of the tip section 72a is 6.68 mm or 20 French, and the interior diameter is 5.08 mm. The intravascular length of the tip section 72a in a preproduction version is 5.88 cm, which is a desirable length to ensure adequate seating within the artery.

The intermediate section 72b has a length of about 5 cm, with an interior diameter that tapers to about 9.27 mm, and with an exterior diameter which tapers from the tip end of about 8.4 mm and increases to about 12-13 cm. Thus, it can be seen that there is a significant exterior diameter change from the tip section 72a to the tip end of the intermediate section 72b. This diameter change forms an annular shoulder 72e adapted to engage the exterior of an artery. That shoulder is formed at an angle of approximately 45° with respect to a diametrical plane through the cannula. It has been found that this angle is particularly desirable for sealing with the exterior of the femoral artery when the cannula is inserted in the direction towards the heart.

Due to the angled shoulder and the angle at which the cannula tip is inserted in the femoral artery, it is important the cannula be rotationally oriented properly. Thus, for orientation purposes, there is formed an elongated orientation rib 72g on the exterior of sections 72b and 72d extending from the suture ring 72c to the proximal end of the body which mates with the fitting 68. The section 72d is about 19 cm in length, making the overall length of the cannula about 33 cm. The interior and exterior diameters are constant with the end of section 72b.

A pair of suture wings or flaps 74 are formed integral with and extend outwardly from the cannula exterior section 72d. The wings have a lower surface which is approximately tangent with the exterior of the section 72d. The suture wings in a prototype are positioned about 5 cm from the suture ring 72c.

Referring to FIGS. 12 and 13, the stylet 66 is an elongated flexible tubular element preferably made of polyvinyl chloride. The stylet 66 is slightly longer than the cannula 12 having a tapered tip 66a on one end which extends beyond the tip of the cannula when the stylet is fully inserted therein. The overall length is about 42 cm. A knob 76 on the other end of the stylet extends beyond the fitting 68 and is useful for installing and removing the stylet from the cannula. The diameter of the stylet is slightly smaller than the inner diameter of the tip of the cannula. A small diameter lumen 77 is formed throughout the length of the stylet and is adapted to receive a small diameter guidewire. Included on the stylet 66 is a cylindrical stop 66b having an exterior diameter which is sized to slide relatively easily within the cannula, but nevertheless there is resistance to movement caused by the stop 76b engaging the interior of the cannula. The stop 76b is spaced from the tip end of the stylet about 15 cm and has a length of about 4 cm. This means that the end of the stop 76b closest to the tip 66a of the stylet is located at the suture ring of the cannula when the stylet is fully inserted in the cannula, as seen in FIG. 16.

Also included in the cannula assembly is an antibackflow ring 80 preferably made of medical-grade silicone rubber. The ring has a short barrel-like tubular shape with two axially spaced outwardly extending annular ribs 80a and 80b. The ribs are dimensioned such that they snugly engage the interior wall of the fitting 68 or cannula 12 and the exterior of the stylet to form a liquid inner and outer seal.

Mounted on the exterior of the cannula between the suture wings and the fitting 68 is the adjustable medical clamp 71. The clamp is of standard construction, adapted to be manually set to pinch the cannula closed when the stylet is removed.

In use, the guidewire is inserted into the femoral artery followed by the cannula and stylet with the stylet fully inserted, as shown in FIGS. 10, 11 and 15. The cannula is preferably introduced by use of the Seldinger technique, or a cutdown procedure along with vessel dilation. The assembly, guided by the guidewire, is inserted to the point where the cannula angled shoulder 72e engages the exterior of an artery 82 with the cannula tip section 72a extending into the artery, together with the tip of the stylet, as illustrated in FIG. 15. It can be seen from that figure that the angled shoulder 72e engages the artery in a manner such that the artery substantially conforms to the shoulder with the exterior of the artery to form a seal, and limits insertion. With the cannula so positioned, it is sutured to the leg by means of the wings, as shown in FIG. 15.

With the cannula so positioned, there is little blood leakage through the hole in the artery as a result of the seal with the shoulder 72e. Also, the backflow ring 80 prevents leakage through the annular passage between the stylet and the cannula, as seen in FIG. 10. With the forward portion of the cannula relatively firmly positioned on the patient's leg, the other end of the cannula is free to be raised or manipulated, as may be appreciated from FIGS. 10 and 11.

When it is desirable to connect the cannula to an extracorporeal circuit, the stylet 66 is partially withdrawn by pulling on the knob 76 to the position shown in FIG. 17, wherein the stop 66b on the stylet engages anti-backflow ring 80 in the fitting. There is firm resistance to withdrawing the ring 80 out of the cannula so that an operator recognizes that is the point to stop. The tip 66a of the stylet is spaced considerably from the suture ring since the length of the stylet from the stop 66b to its tip 66a is somewhat less than the length of the cannula from its fitting end to the suture ring 72c. As the stylet 66 is withdrawn, a small quantity of blood enters the cannula, limited by the volume displaced by the stylet. With the stylet stop engaging the ring 80, the clamp 71 is squeezed onto the cannula section 72d at a location between the tip 66a of the stylet and the suture ring 72c, as seen in FIG. 17. By locating the clamp close to the tip 66a of the stylet, there is only a small quantity of blood between the clamp and the stylet stop. Once the clamp has been positioned, and closed, the stylet can be withdrawn completely with a pulling force greater than that to previously move the stylet, such that the ring 80 in the end of the fitting is also withdrawn. The ring 80 remains captured on the stylet 66. At this stage, there is only a small quantity of blood in the open end of the cannula, and it is not under pressure. Because of this and the suture wings, the end of the cannula can be easily handled for making connections to the pump and priming this cannula without loss of blood.

REPERFUSION CATHETER

The reperfusion catheter 16 is preferably made from flexible polyvinylchloride (PVC) tubing, preferably in the range of 3.5 to 5 French. The catheter 16 include a female luer lock fitting (not shown) at the proximal end. Preferably, the PVC tubing is barium impregnated or incorporates two radiopaque bands for locating purposes, one of such bands being located at 61 in FIG. 19. The reperfusion catheter 16 has a distal end 58 which contains a plurality of apertures 60 oriented in a spiral along the longitudinal axis of the catheter 16. The holes are about 0.030 inch (0.762 mm) and extend for a tip length of about 2 cm. The tip of the catheter 16 tapers to a reduced size of about 3 French (0.039 inch, 0.91 mm).

In installing the coronary reperfusion catheter 16, there is first inserted a flexible guidewire 34, such as 0.018 inch diameter, which is capable of being inserted through the occlusion in the heart. A guiding catheter 62 is inserted onto the guidewire 34 to a point just short of the coronary ostium. The catheter 16 is inserted onto the guidewire 34 and into the guide catheter 62. Once the smaller reperfusion catheter 16 is positioned with its distal end 58 beyond the occlusion, the guidewire 34 is withdrawn, and the reperfusion solution can be passed through the catheter 16 to exit through the apertures 60. The tapered tip of the catheter facilitates penetration of the blockage and forms a seal with the blockage to prevent blood flow through the occlusion.

SYSTEM OPERATION

The application of the above system and method will now be described with respect to FIG. 1. A heart attack victim has a heart/lung bypass initiated by cannulating the femoral artery by arterial cannula 12 for arterial inflow, and by cannulating the femoral vein by the venous catheter 10 and advancing it under fluoroscopic control into the right atrium for venous return. The femoral-femoral bypass is sustained by the above-identified apparatus.

The left ventricular vent catheter 14 is inserted through the femoral artery through the aortic valve, and into the left ventricle to provide left ventricular decompression. The vent catheter 14 maintains the heart in an at-rest condition by removing all blood flowing into the left ventricle. The process of the heart attack has been slowed markedly by placing the heart in such at-rest condition.

The reperfusion catheter 16 is inserted as outlined above to administer a regional blood cardioplegia distal to the site of the occlusion which precipitated the heart attack. After reperfusion therapy, the occlusion which caused the heart attack is then dissolved by thrombolytic agents or by balloon angioplasty. The reperfusion catheter 16 or the guide catheter 62 may advantageously be used for these methods of removing the occlusion. Once the reperfusion is completed, a guidewire is reinserted through it and the reperfusion catheter 16 is removed. An angioplasty catheter is then advanced in the guide catheter and conventional angioplasty is performed to relieve the stenosis in the coronary artery which caused a clot to form. The guidewire, angioplasty catheter are removed and, after an additional 30 minutes on total bypass the catheter 14 is withdrawn. The catheters 14, 16 are withdrawn and blood is allowed to enter the left ventricle. The patient can then be taken off the heart bypass system. If the closed artery cannot be penetrated, the patient can be transported to the operating room for coronary bypass grafting around the blockage.

The above procedure, whereby normal blood is excluded from the area of the injured myocardium until after a period of reperfusion, has been shown in animal tests to lead to the consistent recovery of 40-100% of the muscle function when the treatment is given within four to six hours of the occlusion.

The apparatus and procedure thus offer the possibility of allowing greatly improved, if not complete, recovery by heart attack victims who would otherwise suffer from reduced heart function and shortened life span because a portion of the myocardium necrosed from the prolonged absence of blood.

Another advantage is provided by the use of one pump for both the venous catheter 10 and the vent catheter 14. The single pump greatly simplifies the system operation, and requires less personnel, with less training, to maintain the appropriate blood pressure in the heart attack victim, while adequately venting the heart.

The system further advantageously lends itself to electronic and mechanical control systems uniquely designed for performance of total extracorporeal circulation and controlled coronary reperfusion.

While the above description is of the preferred embodiment, the disclosure will suggest or render apparent various modifications and variations to those skilled in the art which are within the spirit and scope of the subject invention.

I claim:

1. An extracorporeal bypass apparatus, comprising:
   a venous catheter for insertion into a femoral vein, such catheter being sufficiently long and flexible to reach the atrium area of a patent's heart;
   an arterial cannula;
   a single pump connected between the venous catheter and the arterial cannula for withdrawing blood from a patient through said venous catheter and pumping it into a patient through the arterial cannula; and
   a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter,
   said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed;
   said vent catheter being a thin-walled flexible tube which has a coiled distal end, which is adapted to conform to a guide wire used in inserting the vent catheter.

2. An extracorporeal bypass apparatus, comprising:

a venous catheter for insertion into a femoral vein, such catheter being sufficiently long and flexible to reach the atrium area of a patent's heart;

an arterial cannula;

a single pump connected between the venous catheter and the arterial cannula for withdrawing blood from a patient through said venous catheter and pumping it into a patient through the arterial cannula; and a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter;

said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed;

said vent catheter including a plurality of apertures in the side wall of its distal end, and said vent catheter including a pressure lumen extending from the proximal end of the vent catheter to an inlet adjacent said apertures, the apertures being between the tip of the vent catheter and the inlet to the pressure lumen.

3. An extracorporeal bypass apparatus, comprising:

a venous catheter for insertion into a femoral vein, such catheter being sufficiently long and flexible to reach the atrium area of a patent's heart;

an arterial cannula;

a single pump connected between the venous catheter and the arterial cannula for withdrawing blood from a patient through said venous catheter and pumping it into a patient through the arterial cannula; and a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter, said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed;

said vent catheter having a flexible coiled distal end which presents an exterior curved surface to the aortic valve when the tip of the vent catheter is to be inserted into the ventricle, and said coiled end being adapted to fit totally within the ventricle.

4. An extracorporeal bypass apparatus, comprising:

a venous catheter for insertion into a femoral vein, such catheter being sufficiently long and flexible to reach the atrium area of a patent's heart;

an arterial cannula;

a single pump connected between the venous catheter and the arterial cannula for withdrawing blood from a patient through said venous catheter and pumping it into a patient through the arterial cannula;

a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter, said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed; and a reservoir having an inlet in communication with the output of said pump and having an outlet in communication with the connection between said venous cannula and said pump, and including means for adjusting the flow of liquid into and out of said reservoir.

5. An extracorporeal bypass apparatus, comprising:

a venous catheter for insertion into a femoral vein, such catheter being sufficiently long and flexible to reach the atrium area of a patent's heart;

an arterial cannula;

a single pump connected between the venous catheter and the arterial cannula for withdrawing blood from a patient through said venous catheter and pumping it into a patient through the arterial cannula;

a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter, said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed; and a blood cardioplegia delivery system, comprising:

a cardioplegia delivery pump having an inlet connected to the output of said arterial pump;

a source of cardioplegic liquid connected as an input to said cardioplegia pump; and a coronary reperfusion catheter assembly including a catheter connected to the output of said cardioplegia pump, the coronary reperfusion catheter being sufficiently long and flexible to be adapted to be inserted through a patient's artery to reach an area of the heart that has been deprived of blood so that a cardioplegia solution can be applied to that area before resuming normal blood flow.

6. The apparatus of claim 5, wherein said reperfusion catheter assembly includes a guidewire adapted to guide the reperfusion catheter through said area, and a guide catheter through which said reperfusion catheter is inserted in reaching a point just short of said area.

7. The apparatus of claim 5, wherein said venous catheter is made of ethylene-vinyl-acetate material with a thin-walled construction that resists kinking.

8. An extracorporeal bypass apparatus, comprising:
a venous catheter for insertion into a femoral vein, such catheter being sufficiently long and flexible to reach the atrium area of a patent's heart;
an arterial cannula;
a single pump connected between the venous catheter and the arterial cannula for withdrawing blood from a patient through said venous catheter and pumping it into a patient through the arterial cannula;
a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter,
said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed; and
said arterial cannula comprising an elongated tube having a tip section adapted to be inserted into the femoral artery, said tube having a shoulder adjacent to said tip section adapted to engage the exterior of the artery to limit insertion of the tip section into the artery and to form a seal at the exterior of the artery.

9. The apparatus of claim 8, wherein the surface of said shoulder which engages the artery is formed at an angle of approximately 45° with respect to the diameter of the cannula.

10. The apparatus of claim 9, including a pair of suture wings extending outwardly from the exterior of the cannula and adapted to be sutured to a patient's skin so as to maintain the cannula tip section properly in the artery while leaving the proximal end of the cannula outwardly from the wings to be easily manipulated.

11. The apparatus of claim 8, including a stylet adapted to fit within the cannula, said stylet including a stop on its exterior which slides within the cannula.

12. The apparatus of claim 11, including an antibackflow ring positioned in the proximal end of the cannula or a fitting connected to the cannula and slidably receiving the stylet, the ring sealing the cannula and being engaged by the stylet stop as the stylet is being withdrawn, but the ring being removable from the cannula by an increased pulling force on the stylet.

13. An extracorporeal bypass apparatus, comprising:
a venous catheter for insertion into a femoral vein, such catheter being sufficiently long and flexible to reach the atrium area of a patent's heart;
an arterial cannula;
a single pump connected between the venous catheter and the arterial cannula for withdrawing blood from a patient through said venous catheter and pumping it into a patient through the arterial cannula;
a vent catheter for insertion into an artery sufficiently long and flexible to reach the left ventricle of the heart, said vent catheter being connected in parallel with the venous catheter connected to the pump in a manner such that the negative pressure developed by said pump is applied to the venous catheter and the vent catheter,
said venous catheter and said pump being constructed such that substantially all of the patient's blood which would normally be returned to the heart is bypassed through the venous catheter, and the blood reaching the left ventricle of the heart is withdrawn through the vent catheter so that the ventricle is decompressed; and
a stylet slidably positioned in the cannula and a removable seal extending between the interior of the cannula and the stylet so that, if the tip of the cannula is in the artery, the seal prevents liquid flow out of the cannula.

14. An extracorporeal bypass system, comprising:
a venous catheter for insertion into a femoral vein, such catheter being sufficiently long and flexible to reach the right atrium area of a patent's heart;
an arterial cannula;
a pump connected between the venous catheter and the arterial cannula for withdrawing blood from a patient through said venous catheter and pumping it into a patient through the arterial cannula; and
a bridging, non-dynamic reservoir having an inlet connected to the output of said pump in an outlet connected to the inlet of said pump;
whereby said reservoir is connected in parallel with said pump so that blood may be pumped directly from the pump to said arterial cannula without passing through said reservoir and so that said reservoir inlet and outlet can be opened or closed to permit flow into or out of said reservoir.

15. The system of claim 14, including means for controlling the liquid flow through said system to about 5 liters per minute, maintaining the negative pressure on the venous catheter at an amount no greater than about 200 mm Hg.

16. The system of claim 14, including control means for periodically permitting flow into or out of said reservoir.

17. A percutaneous cardiopulmonary bypass apparatus, comprising:
a venous catheter for insertion into a femoral vein;
an arterial cannula for insertion into an artery;
an oxygenator;
a pump connected between the venous catheter and the oxygenator for withdrawing blood from a patient through said venous catheter and pumping it through the oxygenator and the arterial cannula into a patient, said catheter being sufficiently long and flexible to reach the atrium area of a patient's heart, said catheter having an interior diameter large enough to permit blood flow of 7 liters per minute with a negative pressure provided by said pump being no greater than 200 mm Hg, and said catheter being thin-walled, but nonkinkable with normal handling,
said catheter having a plurality of holes in its side wall extending from the distal end of the tip far enough to not only draw blood from the atrium area of the heart, but to also draw blood from the portion of the vein draining in the lower portion of the body.

18. The apparatus of claim 17, wherein said catheter is made of ethylene-vinyl-acetate and has a wall thickness of about 0.825 mm.

19. The apparatus of claim 17, wherein said catheter is made of ethylene-vinyl-acetate having about 18% acetate.

20. The apparatus of claim 17, wherein said catheter is constructed such that it will not collapse when positioned within a patient and subjected to 200 mm of negative pressure.

21. A percutaneous cardiopulmonary bypass apparatus, comprising:
   a venous catheter for insertion into a femoral vein;
   an arterial cannula for insertion into an artery;
   an oxygenator;
   a pump connected between the venous catheter and the oxygenator for withdrawing blood from a patient through said venous catheter and pumping it through the oxygenator and the arterial cannula into a patient, said catheter being sufficiently long and flexible to reach the atrium area of a patient's heart, said catheter having an interior diameter large enough to permit blood flow of 7 liters per minute with a negative pressure provided by said pump being no greater than 200 mm Hg, and said catheter being thin-walled, but nonkinkable with normal handling; and
   said catheter being in the form of two venous catheters one for insertion in a femoral vein and the other for insertion in a second femoral vein, and said two catheters combined permit blood flow up to approximately 7 liters per minute with a negative pressure of no greater than approximately 200 mm Hg.

22. A method for providing a peripheral cardiopulmonary bypass system, comprising:
   inserting a venous catheter into a femoral vein with the tip of the catheter extending to the right atrium area of a patient's heart;
   inserting an arterial cannula into a femoral artery;
   inserting a vent catheter into a femoral artery with the tip of the vent catheter extending to the left ventricle of the heart;
   connecting the two catheters to the input side of a single heart bypass pump and connecting the output of the pump to the arterial cannula;
   pumping substantially all of the patient's venous return blood out of the patient and back into the patient through the femoral artery while withdrawing blood through the vent catheter so as to maintain the ventricle in a decompressed condition; and
   monitoring the negative pressure developed by said pumps so as to maintain the negative pressure with no greater than 200 ml of mercury.

23. The method of claim 22, including monitoring the pressure in the patient's ventricle and adjusting the system as necessary to maintain the ventricle in a decompressed condition and keeping the negative pressure applied to the vent catheter at a safe level.

24. The method of claim 22, including connecting a reservoir to the output of said pump and to the input to said pump, and adjusting controls to and from the reservoir so as to periodically add liquid to the system or remove liquid from the system as needed to maintain the desired flow through the system within the desired pressure range.

25. A method for providing a peripheral cardiopulmonary bypass system, comprising:
   inserting a venous catheter into a femoral vein with the tip of the catheter extending to the right atrium area of a patient's heart;
   inserting an arterial cannula into a femoral artery;
   inserting a vent catheter into a femoral artery with the tip of the vent catheter extending to the left ventricle of the heart;
   connecting the two catheters to the input side of a single heart bypass pump and connecting the output of the pump to the arterial cannula;
   pumping substantially all of the patient's venous return blood out of the patient and back into the patient through the femoral artery while withdrawing blood through the vent catheter so as to maintain the ventricle in a decompressed condition; and
   monitoring the speed of said pump so as to provide a flow in the system of up to 7 liters per minute.

26. A method for providing a cardiopulmonary bypass system, comprising:
   inserting a venous catheter into a femoral vein with the tip of the catheter extending to the right atrium area of a patient's heart;
   inserting an arterial cannula into a femoral artery;
   pumping blood from the venous catheter through a blood oxygenator to the arterial cannula;
   connecting a bridging reservoir in parallel to the pumping means with an inlet to the reservoir being connected to the outlet of the pumping means and with an outlet of the reservoir connected to the inlet of the pump; and
   selectively opening and closing the reservoir inlet and outlet to add or withdraw liquid from the system as needed.

27. The method of claim 26, including inserting a vent catheter into a femoral artery with the tip of the vent catheter extending to the left ventricle of the heart; and applying negative pressure to said vent catheter to decompress the left ventricle.

28. A method for providing a cardiopulmonary bypass system, comprising:
   inserting an arterial cannula into a femoral artery;
   inserting a vent catheter into a femoral artery with the tip of the vent catheter extending to the left ventricle of the heart;
   pumping blood from the vent catheter to the arterial cannula; and
   connecting a reservoir in parallel to the pumping means with an inlet to the reservoir being connected to the outlet of the pumping means and with an outlet of the reservoir connected to the inlet of the pump.

29. The method of claim 28, including selectively opening and closing the reservoir inlet and outlet to add or withdraw liquid from the system as needed.

30. An extracorporeal heart bypass apparatus comprising:
   a venous catheter;
   a positive displacement pump connected to apply negative pressure to said catheter to withdraw blood from a patient;
   a compliance chamber connected between said pump and said catheter to reduce the rate of change of negative pressure applied by said pump on said catheter, said chamber comprising the space between an expandable reservoir connected between said pump and said catheter, and a closed housing surrounding said reservoir whereby the pressure in the chamber is related to the pressure in the reservoir; and
   a controller to control the speed of said pump, said controller being responsive to the pressure in said space so as to decrease pump speed with an increase in negative pressure in the compliance chamber.

31. The apparatus of claim 30, including a pressure transducer sensing the pressure in said space, with the transducer connected to provide its pressure information to said controller.

32. The apparatus of claim 30, wherein said positive displacement pump is a peristaltic pump.

33. The apparatus of claim 30, including a vent catheter connected in parallel to said venous catheter such that the negative pressure provided by said pump is also applied to the vent catheter.

34. The apparatus of claim 30, including a reservoir bridging said pump with said bridging reservoir having controls for increasing or decreasing the volume of fluid in the system; and an arterial cannula for conducting the output of said pump to a patient's artery.

35. A method of controlling negative pressure changes to a patient's venous blood supply in withdrawing blood from a patient in connection with a cardiopulmonary bypass system, comprising:

inserting a venous catheter into a patient's vein;

operating a positive displacement pump to apply a negative pressure to said catheter;

reducing the rate at which negative pressure on said catheter can be changed by said pump so as to keep the negative pressure at a safe level and prevent the nucleation of gas in the blood;

sensing said negative pressure;

changing pump speed in response to sensed pressure changes;

said reducing step including applying the negative pressure of said pump to an expandable reservoir positioned in a conduit between said catheter and said pump, with a housing surrounding the reservoir creating a chamber responsive to changes of said pressures, the volume of blood in said reservoir being reduced upon increases in negative pressure, thereby reducing the rate at which negative pressure can be increased; and said sensing step including sensing the pressure in the chamber between said reservoir and said housing and utilizing the sensed pressure to a said controller to decrease the speed of said pump in response to increases in the negative pressure in said chamber.

* * * * *